(12) United States Patent
Nakamura

(10) Patent No.: US 11,906,294 B2
(45) Date of Patent: Feb. 20, 2024

(54) ALIGNMENT APPARATUS, ALIGNMENT SYSTEM, ALIGNMENT METHOD, AND RECORDING MEDIUM

(71) Applicant: Satoshi Nakamura, Chiba (JP)

(72) Inventor: Satoshi Nakamura, Chiba (JP)

(73) Assignee: Ricoh Company, Ltd., Tokyo (JP)

( * ) Notice: Subject to any disclaimer, the term of this patent is extended or adjusted under 35 U.S.C. 154(b) by 254 days.

(21) Appl. No.: 17/373,878

(22) Filed: Jul. 13, 2021

(65) Prior Publication Data

US 2022/0034654 A1    Feb. 3, 2022

(30) Foreign Application Priority Data

Jul. 28, 2020  (JP) ................................. 2020-127627
Dec. 24, 2020  (JP) ................................. 2020-215728

(51) Int. Cl.
| | | |
|---|---|---|
| G01B 21/20 | (2006.01) | |
| G06T 7/50 | (2017.01) | |
| G01B 21/04 | (2006.01) | |
| A61B 5/055 | (2006.01) | |
| A61B 5/00 | (2006.01) | |

(52) U.S. Cl.
CPC ............. *G01B 21/20* (2013.01); *G01B 21/04* (2013.01); *G06T 7/50* (2017.01); *A61B 5/0042* (2013.01); *A61B 5/055* (2013.01); *G06T 2207/10028* (2013.01)

(58) Field of Classification Search
CPC .......... G01B 21/20; G01B 21/04; G06T 7/50; G06T 2207/10028; A61B 5/0042; A61B 5/055

USPC .......................................................... 702/167
See application file for complete search history.

(56) References Cited

U.S. PATENT DOCUMENTS

| | | | |
|---|---|---|---|
| 6,701,006 B2 * | 3/2004 | Moore ................. | G06V 10/757 382/294 |
| 6,920,242 B1 * | 7/2005 | Moore ................. | G06V 10/757 382/294 |
| 2019/0285397 A1 | 9/2019 | Nakamura et al. | |

FOREIGN PATENT DOCUMENTS

| | | |
|---|---|---|
| JP | 2006-132947 | 5/2006 |
| JP | 2014-169990 | 9/2014 |
| JP | 2019-164109 | 9/2019 |

OTHER PUBLICATIONS

Published by Elsevier Science Ltd, "New Algorithms for 2D and 3D Point Matching: Pose Estimation and Correspondence", Pattern Recognition, vol. 31, No. 8, pp. 1019-1031, 1998.

(Continued)

*Primary Examiner* — Aditya S Bhat
(74) *Attorney, Agent, or Firm* — Harness, Dickey & Pierce, P.L.C.

(57) ABSTRACT

An apparatus, system, method, and a control program on a recording medium are provided, each of which: acquires first point cloud data, and second point cloud data different from the first point cloud data; sets a plurality of search start positions each used for alignment form the first point cloud data to the second point cloud data; searches, for each of one or more of the plurality of search start positions, a solution candidate for coordinate transformation from the first point cloud data to the second point cloud data, to generate a plurality of solution candidates; and determines a final solution, from the plurality of solution candidates.

20 Claims, 10 Drawing Sheets

(56) References Cited

OTHER PUBLICATIONS

Paul J. Besl, Member, IEEE, and Neil D. Mckay, "A Method for Registration of 3-D Shapes", IEEE Transactions on Pattern Analysis and Machine Intelligence, vol. 14. No. 2, Feb. 1992.

Yanghai Tsin and Takeo Kanade, "A Correlation-Based Approach to Robust Point Set Registration", T. Pajdla and J. Matas (Eds.): ECCV 2004, LNCS 3023, pp. 558-569, 2004.

* cited by examiner

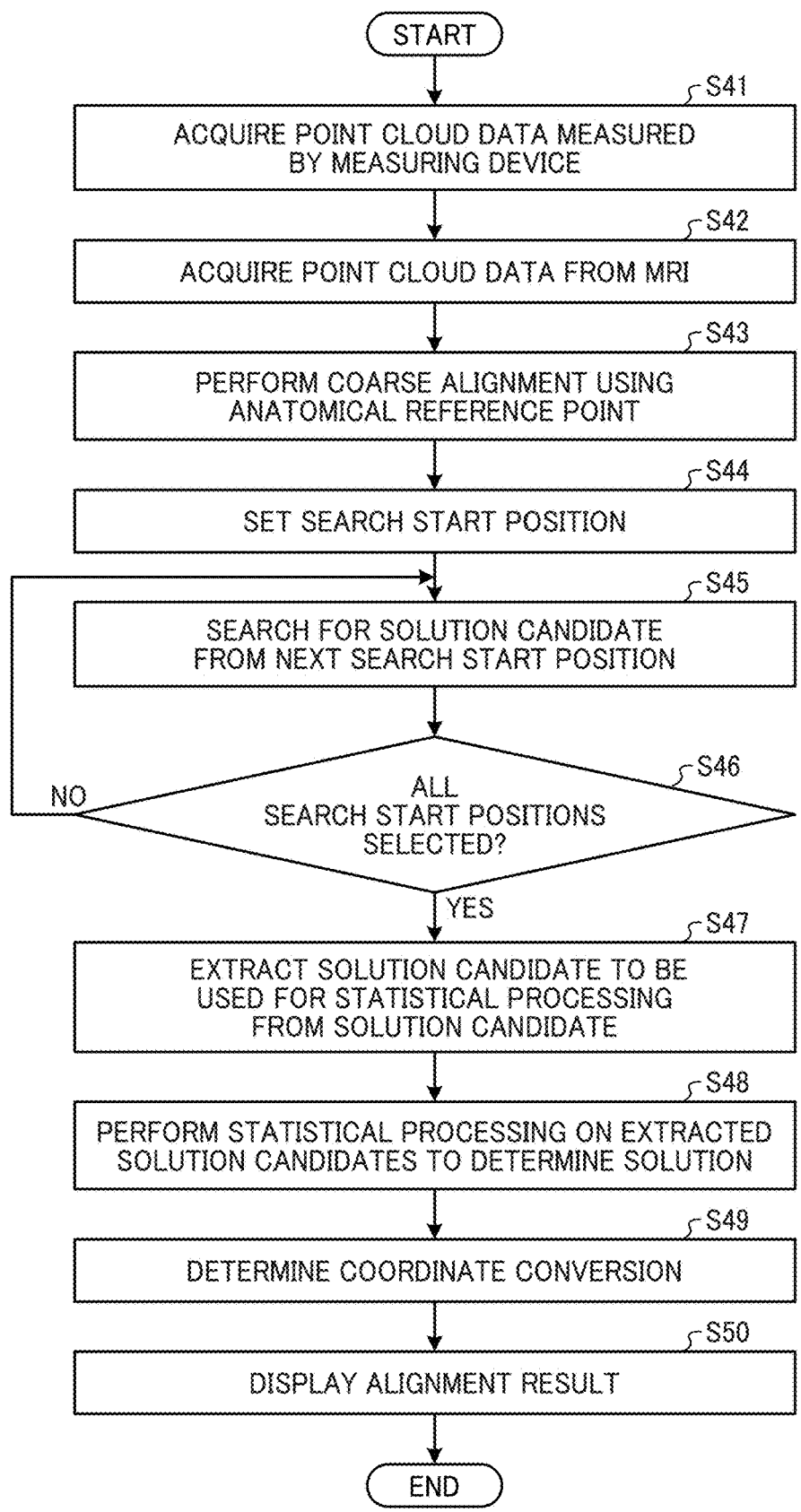

ALIGNMENT APPARATUS, ALIGNMENT SYSTEM, ALIGNMENT METHOD, AND RECORDING MEDIUM

CROSS-REFERENCE TO RELATED APPLICATIONS

This patent application is based on and claims priority pursuant to 35 U.S.C. § 119(a) to Japanese Patent Application Nos. 2020-127627, filed on Jul. 28, 2020, and 2020-215728, filed on Dec. 24, 2020, in the Japan Patent Office, the entire disclosure of which is hereby incorporated by reference herein.

BACKGROUND

Technical Field

The present disclosure relates to an alignment apparatus, an alignment system, an alignment method, and a recording medium.

Related Art

In the field of three dimensional space measurement and the field of multi-modal integration, a plurality of three dimensional point cloud data are aligned to perform coordinate transformation between the respective point cloud data. Here, the three dimensional point cloud data (hereinafter, referred to as point cloud data) is a set of data points that represents an object, generated based on image data, distance data, or the like of the object obtained by a measuring device. In the field of three dimensional space measurement, point cloud data measured at different times using the same measuring device are used to align for registration. In the field of multi-modal integration, point cloud data measured at the same time or different times using different measuring devices are used to align for registration. Although various algorithms have been proposed for alignment of the point cloud data, it is generally conceived as a minimization problem of an error function for evaluating the aligned state.

However, a large number of local solutions generally exist in the solution space of the minimization problem of the error function (more broadly, the objective function). For this reason, the search for a solution tends to be limited to a local solution, and a suitable solution is not necessarily found. In order to alleviate this problem, various techniques have been proposed, such as a technique to change a search start position, or a technique to randomly displace a solution candidate found when an error function converges for re-search. The above-described techniques are effective, when the error function matches the objective function (that is, in a case where the alignment between point cloud data itself is the objective). Such cases include, for example, when connection between the point clouds in the three dimensional space measurement is to be performed. In contrary, the above-described techniques may not be effective, in a case where the error function is different from the objective function (for example, in the case where an object is to derive a coordinate transformation between coordinate systems in which point cloud data exists). Such cases include, for example, a case where a coordinate transformation obtained by alignment between point cloud data is applied to another point cloud data.

SUMMARY

Example embodiments include an apparatus, system, and method, each of which: acquires first point cloud data, and second point cloud data different from the first point cloud data; sets a plurality of search start positions each used for alignment from the first point cloud data to the second point cloud data; searches, for each of one or more of the plurality of search start positions, a solution candidate for coordinate transformation from the first point cloud data to the second point cloud data, to generate a plurality of solution candidates; and determines a final solution, from the plurality of solution candidates.

Example embodiments include a non-transitory recording medium storing a control program for causing a computer system to carry out the above-described method.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 11 is a flowchart illustrating an example alignment process, performed by the alignment apparatus, according to the fourth embodiment.

Figure 1:
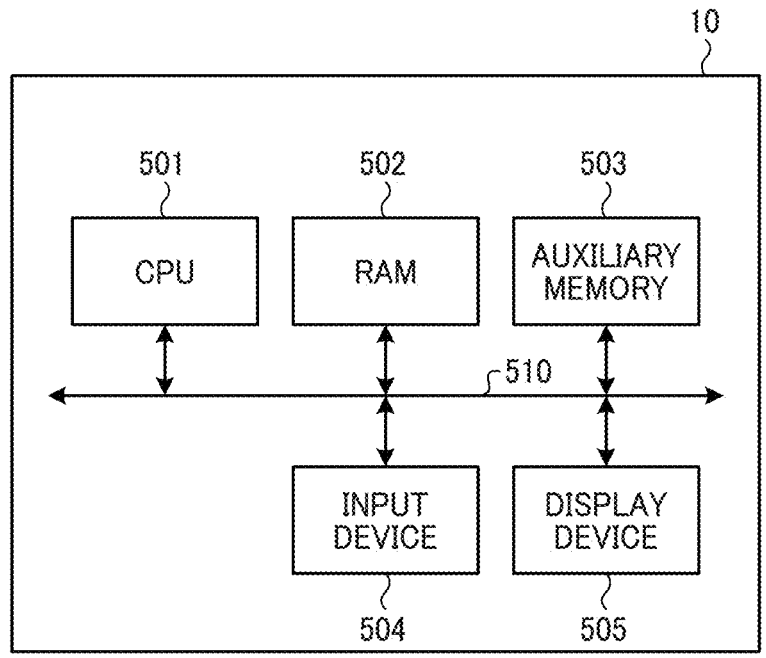
FIG. 1 is a diagram illustrating an example hardware configuration of an alignment apparatus according to a first embodiment.

The accompanying drawings are intended to depict embodiments of the present invention and should not be interpreted to limit the scope thereof. The accompanying drawings are not to be considered as drawn to scale unless explicitly noted. Also, identical or similar reference numerals designate identical or similar components throughout the several views.

DETAILED DESCRIPTION

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Referring now to the drawings, embodiments of the present disclosure are described below. As used herein, the singular forms "a," "an," and "the" are intended to include the plural forms as well, unless the context clearly indicates otherwise.

Hereinafter, an alignment apparatus, an alignment system, an alignment method, and a program stored in a non-transitory recording medium according to the present disclosure will be described with reference to the drawings. The present invention, however, is not limited to the following embodiment, and the constituent elements of the following embodiment include those that can be easily conceived by those skilled in the art, those being substantially the same ones, and those being within equivalent ranges. Furthermore, various omissions, substitutions, changes and combinations of the constituent elements can be made without departing from the gist of the following embodiments.

In this disclosure, computer software (hereinafter simply referred to as "software") is a program relating to operation to be performed by a computer or any data to be used in processing by a computer according to such program. The application program, which may be simply referred to as "application", is a general term for any software used to perform certain processing. The operating system (hereinafter simply referred to as an "OS") is software for controlling a computer, such that software, such as application, is able to use computer resource. The OS performs basic management and control of the computer, such as control of input and output, management of hardware such as a memory and a hard disk, and control of processes. The application controls processing using functions provided by the OS. The program is a set of instructions for causing the computer to perform processing to have a certain result. While data to be used in processing according to the program is not a program itself, such data may define processing to be performed by the program such that it may be interpreted as equivalent to the program. For example, a data structure, which is a logical structure of data described by an interrelation between data elements, may be interpreted as equivalent to the program.

First Embodiment

Hardware Configuration of Alignment Apparatus

FIG. 1 is a diagram illustrating an example hardware configuration of an alignment apparatus according to a first embodiment of the present invention. Referring to FIG. 1, a hardware configuration of an alignment apparatus 10 according to the present embodiment will be described.

The alignment apparatus 10 illustrated in FIG. 1 is an information processing apparatus that performs alignment processing of a plurality of point cloud data. The alignment apparatus 10 may be implemented by, for example, an information processing apparatus such as a personal computer (PC), a workstation, or a tablet terminal. As illustrated in FIG. 1, the alignment apparatus 10 includes a central processing unit (CPU) 501, a random access memory (RAM) 502, an auxiliary memory 503, an input device 504, and a display device 505.

The CPU 501 is an arithmetic unit that controls entire operation of the alignment apparatus 10.

The RAM 502 is a volatile memory, which may be used as a work area for the CPU 501, for example, to temporarily store the point cloud data read from the auxiliary memory 503.

The auxiliary memory 503 is, for example, a storage device such as a hard disk drive (HDD) or a solid state drive (SDD), which stores three dimensional point cloud data of a measurement target object, a program to be executed by the CPU 501, etc.

The input device 504 is, for example, a keyboard for inputting characters, numbers, and various instructions, and a mouse for selecting and executing various instructions, selecting a processing target, moving a cursor, etc.

The display device 505 is a display, which may be implemented by a liquid crystal display or an organic electro-luminescence (EL) display, and displays various information such as a cursor, a menu, a window, a character, an image, or an alignment result of point cloud data.

The CPU 501, the RAM 502, the auxiliary memory 503, the input device 504, and the display device 505 are communicably connected to each other by a bus 510 such as an address bus and a data bus.

The hardware configuration of the alignment apparatus 10 illustrated in FIG. 1 is just one example, and the alignment apparatus 10 may not include all of the components illustrated in FIG. 1, or may include any other hardware components. For example, the alignment apparatus 10 may additionally include a read only memory (ROM) that stores a program (for example, Basic Input/Output System (BIOS)) for the alignment apparatus 10, a DVD drive for reading from and writing to a Digital Versatile Disk ROM (DVD-ROM) as an example of a removable storage medium, a flash memory, or a network interface (I/F) for communicating data with an external apparatus.

The alignment apparatus 10 is not limited to the single information processing apparatus illustrated in FIG. 1, and may be configured by a plurality of network-based apparatuses such as a plurality of information processing apparatuses.

Functional Configuration and Operation of Alignment Apparatus

Figure 2:
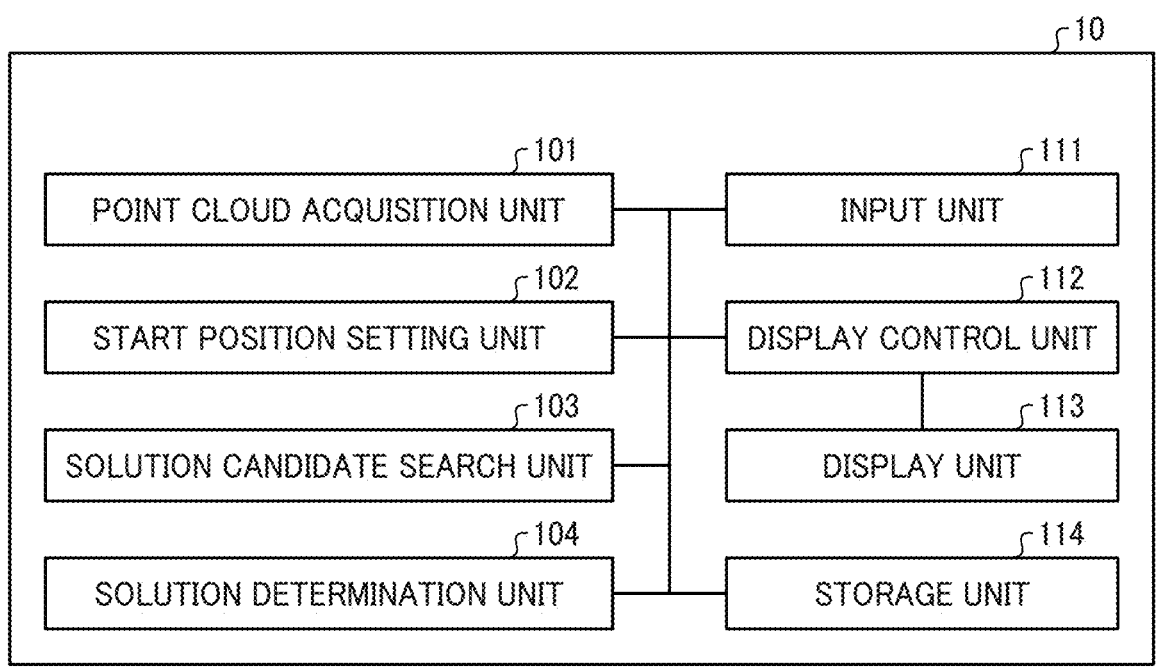
FIG. 2 is a diagram illustrating an example functional configuration of the alignment apparatus according to the first embodiment.
Figure 3A:
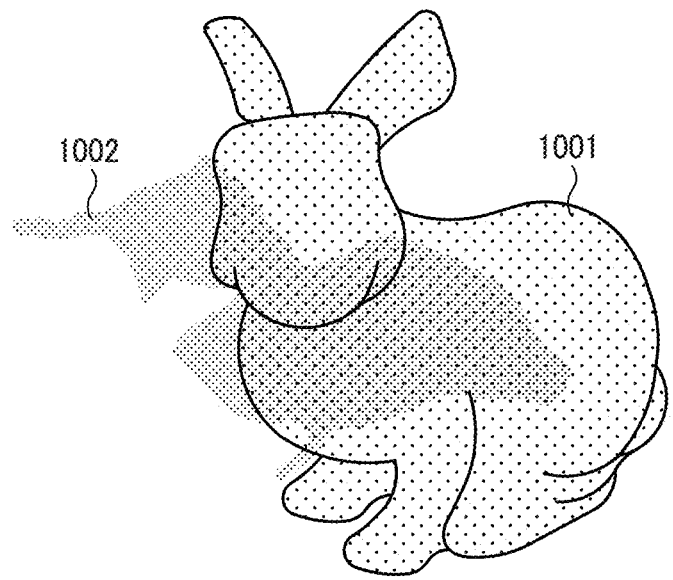
FIGS. 3A and 3B (FIG. 3) are diagrams for explaining alignment of point cloud data.
Figure 3B:
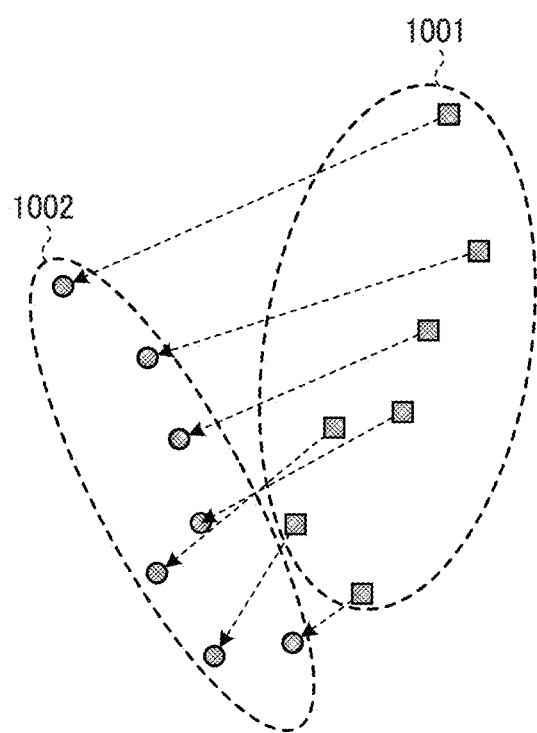

FIG. 2 is a diagram illustrating an example functional configuration of the alignment apparatus according to the first embodiment. FIGS. 3A and 3B (FIG. 3) are diagrams for explaining alignment of point cloud data. The functional configuration and operation of the alignment apparatus 10 according to the present embodiment will be described with reference to FIGS. 2 and 3.

As illustrated in FIG. 2, the alignment apparatus 10 includes a point cloud acquisition unit 101 (acquisition unit), a start position setting unit 102 (position setting unit), a solution candidate search unit 103 (search unit), a solution determination unit 104, an input unit 111, a display control unit 112, a display unit 113, and a storage unit 114.

The point cloud acquisition unit 101 is a functional unit that reads and acquires, from the storage unit 114, two sets of point cloud data of the same object used for alignment. In this disclosure, alignment refers to a process of estimating positions of a plurality of points in the point cloud data representing a three dimensional model of an object, and obtaining such as a displacement amount and a rotation amount for each of the points to align the positions of corresponding points.

For example, as illustrated in FIG. 3A, it is assumed that there are two sets of point cloud data 1001 and 1002 representing a shape of the same animal as an object. As illustrated in FIG. 3B, for each of point in the point cloud data 1001 and point in the point cloud data 1002, points corresponding to each other are identified. Then, any one of a displacement amount, a rotation amount, and a magnification factor, for aligning the position of one point with the position of the corresponding other point are obtained. Accordingly, the point cloud data 1001 and the point cloud data 1002 can be matched (i.e., aligned) with each other.

The point cloud acquisition unit 101 is implemented by a program executed by the CPU 501 of FIG. 1.

The start position setting unit 102 is a functional unit that sets a plurality of search start positions, each of which is a position that search is started for alignment of two sets of point cloud data. That is, one point cloud data (first point cloud data) of the two point cloud data acquired by the point cloud acquisition unit 101 is aligned to the other point group data (second point cloud data). For example, the start position setting unit 102 may set, as the search start position, a position indicated by a user operation input via the input unit 111. In this case, improvement in accuracy is expected, depending on how accurate the position set by the user can be.

In another example, the start position setting unit 102 may set a plurality of search start positions, such that each search start position is added with offset having a preset step size with reference to the original position of the point cloud data before alignment. Accordingly, the search start positions can be arranged evenly, and variations in the search start positions can be reduced. With this even arrangement, the user can instantly recognize each search start position. This further allows thorough search, such that a suitable solution can be stably obtained. The search start position may be offset by parallel movement or by rotation. Specifically, in a case of parallel movement, an amount of displacement in the vertical, horizontal, or longitudinal direction may be given to determine offset. In a case of rotation, the degree of rotation for each coordinate axis may be given to determine offset. Alternatively, the above-described step size may be determined according to a user operation input via the input unit 111. Further, the start position setting unit 102 may set a plurality of search start positions by randomly shifting the position of each search start position with reference to the position of the point cloud data before alignment, for example. In this case, since the search start position is automatically set, operation input by the user can be eliminated. Thus, the initial value dependency of the alignment algorithm can be relaxed. The start position setting unit 102 stores the search start position, which is set, in the storage unit 114. The start position setting unit 102 is implemented by, for example, a program executed by the CPU 501 illustrated in FIG. 1.

The solution candidate search unit 103 is a functional unit that searches for a solution candidate by performing alignment using a preset alignment algorithm, starting from the search start position set by the start position setting unit 102. Here, the solution candidate is a candidate of a displacement vector and a rotation matrix for aligning (that is, applying coordinate transformation to) each point of one point cloud data to corresponding point of the other point cloud data. Specifically, the solution candidate search unit 103 searches for a solution candidate that minimizes an objective function such as an error function by performing alignment using the alignment algorithm from the search start position. The solution candidate search unit 103 stores, in the storage unit 114, the searched solution candidate and the value of the objective function such as the error function in association with each other. The searched solution candidate may be one or more candidates, desirably, a plurality of candidates. In the following description, it is assumed that the objective function is an error function relating to an error in alignment of two sets of point cloud data. In this disclosure, any algorithm can be used as the alignment algorithm, such as an iterative closest point (ICP) algorithm, a robust point matching method, or kernel correlation. The solution candidate search unit 103 is implemented by a program executed by the CPU 501 illustrated in FIG. 1, for example.

The solution determination unit 104 is a functional unit that performs statistical processing on the solution candidates searched by the solution candidate search unit 103, and determines a final solution from among the solution candidates.

As the statistical processing, the solution determination unit 104 may determine, as the final solution, an average value obtained by averaging the values of the plurality of solution candidates that are searched and each weighed by a value (error) of the error function, for example. In this case, it is desirable to use a weighting function that gives a larger weight to a solution candidate having a smaller value (error) of the error function. As one technique, the reciprocal of the error or the reciprocal of the squared error may be used as the weight.

In statistical processing, the solution determination unit 104 may determine, as a final solution, a solution candidate having the error function value (error) that is highest in appearance frequently, from among a plurality of solution candidates. It is desirable that the solution determination unit 104 performs processing using the most frequent value in statistical processing. Specifically, for example, from among the plurality of solution candidates, the solution determination unit 104 determines a solution candidate having the highest appearance frequency as a final solution. If the frequency of the solution candidate is almost the same for more than one solution candidate, the solution determination unit 104 may determine a solution based on an average value instead of the most frequent value. This can improve the processing speed in statistical processing. This can also prevent the solution from becoming unstable (the result changes greatly with a slight difference in frequency).

In statistical processing, for example, the solution determination unit 104 may determine, as a final solution, a median value obtained when a plurality of solution candidates are rearranged in order of values (errors) of the error function.

The solution determination unit 104 may use a predetermined statistical process among the above-described statistical processes. Alternatively, the solution determination unit 104 may use a statistical process selected by a user operation input to the input unit 111. The solution determination unit 104 stores the determined final solution in the storage unit 114. The solution determination unit 104 is implemented by a program executed by the CPU 501 illustrated in FIG. 1, for example.

The input unit 111 is a functional unit that receives an operation input from the user. The input unit 111 is implemented by the input device 504 illustrated in FIG. 1.

The display control unit 112 is a functional unit that controls displaying operation of the display unit 113. The display control unit 112 may display the final solution determined by the solution determination unit 104 on the display unit 113. Alternatively, the display control unit 112 may display point cloud data, which is generated by applying coordinate transformation to one of the two point cloud data using the solution determined by the solution determination unit, and the other point cloud data serving as the alignment target, while superimposing one above the other. In this case, when the two sets of point cloud data are displayed one above the other, it is desirable that the display control unit 112 displays the two sets of point cloud data in different colors. The user can then determine whether the solution (coordinate transformation) determined by the solution determination unit 104 is acceptable or not. The display control unit 112 is implemented by, for example, a program executed by the CPU 501 illustrated in FIG. 1.

The display unit 113 is a functional unit that displays various data and images under control of the display control unit 112. The display unit 113 is implemented by the display device 505 illustrated in FIG. 1.

The storage unit 114 is a functional unit that stores various data such as the three dimensional point cloud data of the measurement target object, the search start positions set by the start position setting unit 102, the solution candidates searched by the solution candidate search unit 103 and each associated with the value of the objective function (error function or the like), and the final solution determined by the solution determination unit 104. The storage unit 114 is implemented by at least one of the RAM 502 and the auxiliary memory 503 illustrated in FIG. 1. The storage unit 114 may be implemented by, for example, a flash memory or a DVD-drive, instead of the RAM 502 or the auxiliary memory 503.

At least one of the point cloud acquisition unit 101, the start position setting unit 102, the solution candidate search unit 103, the solution determination unit 104, and the display control unit 112 may be implemented by an integrated circuit such as an application specific integrated circuit (ASIC) or a field-programmable gate array (FPGA).

FIG. 2 is a conceptual diagram illustrating functional units of the alignment apparatus 10, such that the functions of the alignment apparatus 10 is not limited to such configuration. For example, any combination of functional units, each described as an independent functional unit, in the alignment apparatus 10 illustrated in FIG. 2 may be configured as one functional unit. Alternatively, functions performed by one functional unit of the alignment apparatus 10 illustrated in FIG. 2 may be divided into a plurality of functions to constitute a plurality of functional units.

Alignment Processing of Alignment Apparatus

Figure 4:
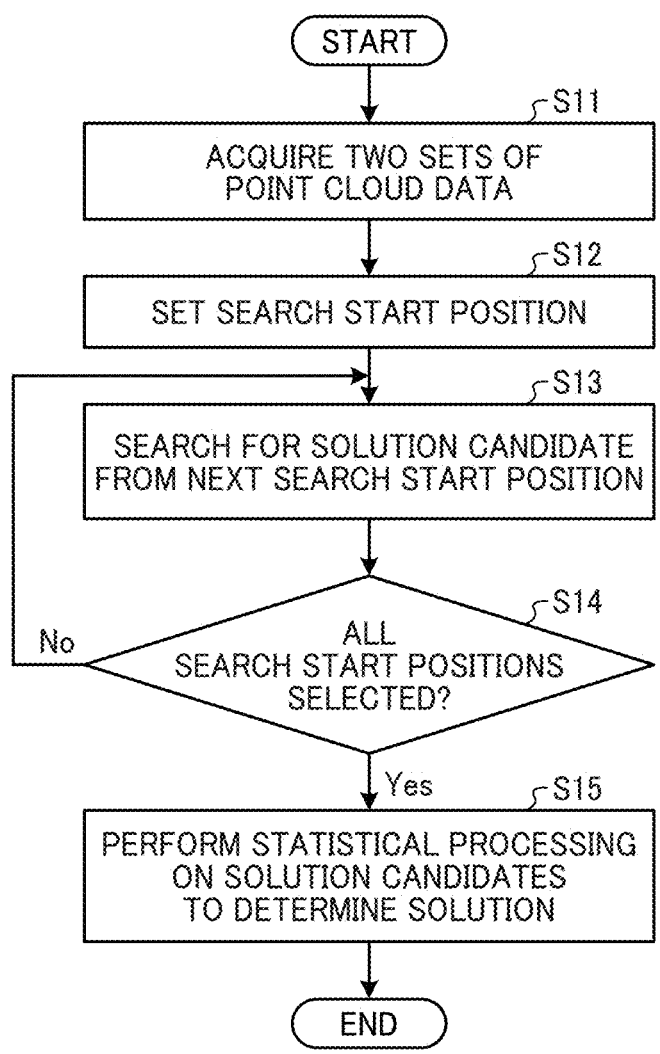
FIG. 4 is a flowchart illustrating an example alignment process, performed by the alignment apparatus, according to the first embodiment.

FIG. 4 is a flowchart illustrating an example alignment process, performed by the alignment apparatus, according to the first embodiment. Referring to FIG. 4, alignment processing by the alignment apparatus 10 according to the present embodiment will be described.

Step S11

The point cloud acquisition unit 101 reads and acquires, from the storage unit 114, two sets of point cloud data for the same object, which are to be used for alignment. The operation then proceeds to step S12.

Step S12

The start position selling unit 102 sets a plurality of search start positions, used for alignment between one point cloud data and the other point cloud data of the two sets of point cloud data acquired by the point cloud acquisition unit 101. Then, the start position setting unit 102 stores the set search start positions in the storage unit 114. The operation then proceeds to step S13.

Step S13

The solution candidate search unit 103 reads, from the storage unit 114, a search start position that has not been selected, from among the search start positions set by the start position setting unit 102, and performs alignment starting from the search start position using the preset alignment algorithm to search for a solution candidate. The solution candidate search unit 103 stores, in the storage unit 114, the searched solution candidate and the value of the objective function such as the error function in association with each other. The operation then proceeds to step S14.

Step S14

The solution candidate search unit 103 determines whether all the search start positions stored in the storage unit 114 are selected or search of the solution candidate. When all the search start positions stored in the storage unit 114 are selected for the search of the solution candidate by the solution candidate search unit 103 (step S14: Yes), the operation proceeds to step S15. When there is an unselected search start position (step S14: No), the operation returns to step S13.

Step S15

The solution determination unit 104 performs statistical processing on the solution candidates searched by the solution candidate search unit 103, and determines a final solution from among the solution candidates. The display control unit 112 may display the final solution determined by the solution determination unit 104 on the display unit 113. Alternatively, the display control unit 112 may display point cloud data, generated by applying coordinate transformation to one of the two point cloud data using the solution determined by the solution determination unit 104, and the other point cloud data serving as the alignment target, while superimposing one above the other. The alignment process then ends.

As described above, at the alignment apparatus 10 of the present embodiment, the start position setting unit 102 sets a plurality of search start positions, each being a position to start searching for aligning one point cloud data to the other point cloud data of the two sets of point cloud data. The solution candidate search unit 103 searches for a solution candidate by performing alignment using the preset alignment algorithm, starting from the search start position set by the start position setting unit 102. The solution determination unit 104 performs statistical processing on the solution candidates searched by the solution candidate search unit 103, and determines a final solution from among the solution candidates. With this configuration, a final solution is derived by applying statistical processing to a plurality of solution candidates each obtained by performing alignment from each of a plurality of search start positions. As a result, a solution can be obtained that is more stable and preferable than a solution that can be obtained by unconditionally selecting a solution candidate that minimizes an error function. That is, in the alignment between the point cloud data, regardless of whether or not the error function for evaluating the state of the alignment is the same as the objective function for evaluating the suitability of the alignment result for the intended use, the local solution can be avoided, such that the suitable solution is found more stably.

Second Embodiment

The alignment apparatus according to the second embodiment will be described, focusing on differences from the alignment apparatus 10 according to the first embodiment. In the present embodiment, it is assumed that statistical processing is performed on solution candidates, after extracting a predetermined number of solution candidates from among the searched solution candidates. The hardware configuration of the alignment apparatus according to the present embodiment is the same as that of the alignment apparatus 10 according to the first embodiment.

Functional Configuration and Operation of Alignment Apparatus

Figure 5:
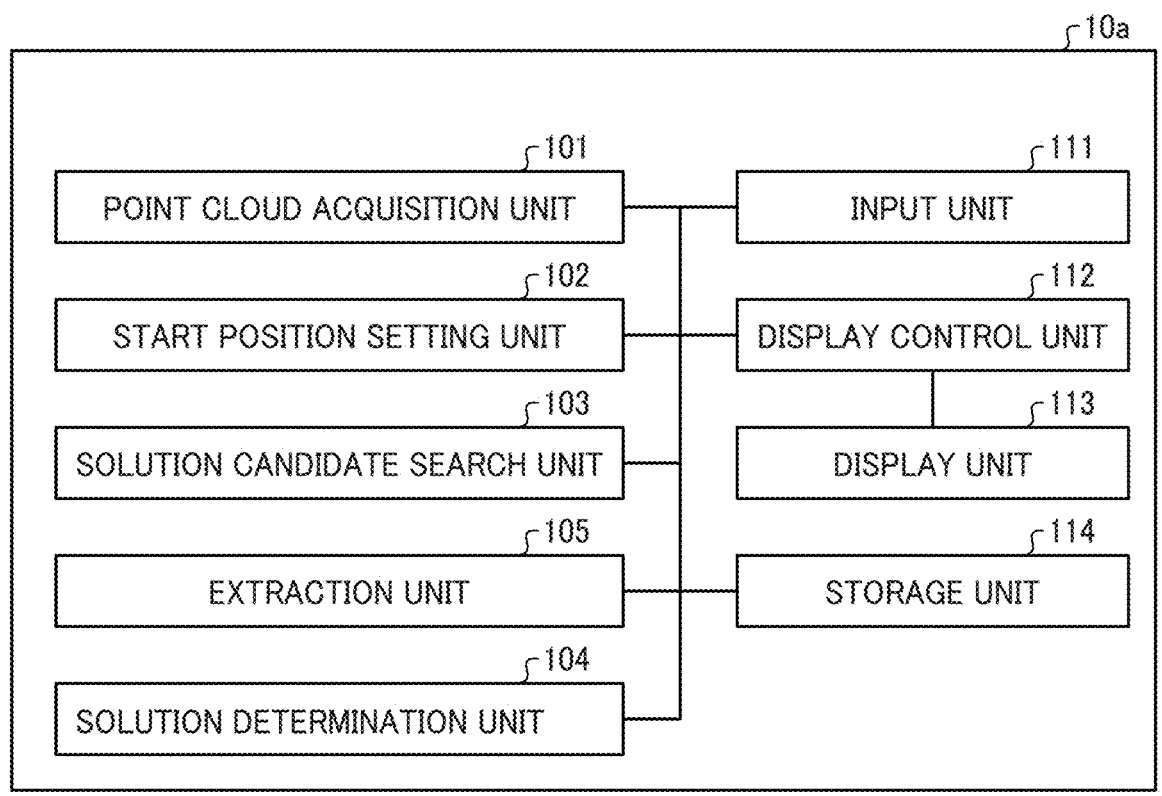
FIG. 5 is a diagram illustrating an example functional configuration of the alignment apparatus according to a second embodiment.

FIG. 5 is a diagram illustrating an example functional configuration of the alignment apparatus 10a according to the second embodiment. The functional configuration and operation of the alignment apparatus 10a according to the present embodiment will be described with reference to FIG. 5.

As illustrated in FIG. 5, the alignment apparatus 10a includes a point cloud acquisition unit 101 (acquisition unit), a start position setting unit 102 (position setting unit), a solution candidate search unit 103 (search unit), an extraction unit 105, a solution determination unit 104, an input unit 111, a display control unit 112, a display unit 113, and a storage unit 114. Of the functional units described above, the functions of the point cloud acquisition unit 101, the start position setting unit 102, the solution candidate search unit 103, the input unit 111, the display control unit 112, the display unit 113, and the storage unit 114 are the same as those described in the first embodiment.

The extraction unit 105 is a functional unit that extracts a predetermined number of solution candidates from among the solution candidates searched by the solution candidate search unit 103. For example, the extraction unit 105 may randomly extract a predetermined number of solution candidates from among the solution candidates searched by the solution candidate search unit 103. Further, the extraction unit 105 may sort the solution candidates searched by the solution candidate search unit 103 in ascending order of values of error, and extract a predetermined number of solution candidates in order from the one having the smallest error until the predetermined number of solution candidates are selected. Further, the extraction unit 105 may obtain frequency of the error for each of solution candidates searched by the solution candidate search unit 103, and extract a predetermined number of solution candidates in order from the one having the highest frequency. The extraction unit 105 is implemented by a program executed by the CPU 501 illustrated in FIG. 1, for example. Further, a number for extraction may be previously set, for example, a user or system administrator.

The solution determination unit 104 is a functional unit that performs statistical processing on the solution candidates extracted by the extraction unit 105, and determines a final solution from among the solution candidates. The statistical processing to be performed on the extracted solution candidates is the same as the processing described above in the first embodiment. The solution determination unit 104 stores the determined final solution in the storage unit 114. The solution determination unit 104 is implemented by a program executed by the CPU 501 illustrated in FIG. 1, for example.

At least one of the point cloud acquisition unit 101, the start position setting unit 102, the solution candidate search unit 103, the extraction unit 105, the solution determination unit 104, and the display control unit 112 may be implemented by an integrated circuit such as an ASIC or FPGA.

FIG. 5 is a conceptual diagram illustrating functional units of the alignment apparatus 10a, such that the functions of the alignment apparatus 10a is not limited to such configuration. For example, any combination of functional units, each described as an independent functional unit, in the alignment apparatus 10a illustrated in FIG. 5 may be configured as one functional unit. Alternatively, functions performed by one functional unit of the alignment apparatus 10a illustrated in FIG. 5 may be divided into a plurality of functions to constitute a plurality of functional units.

Alignment Processing of Alignment Apparatus

Figure 6:
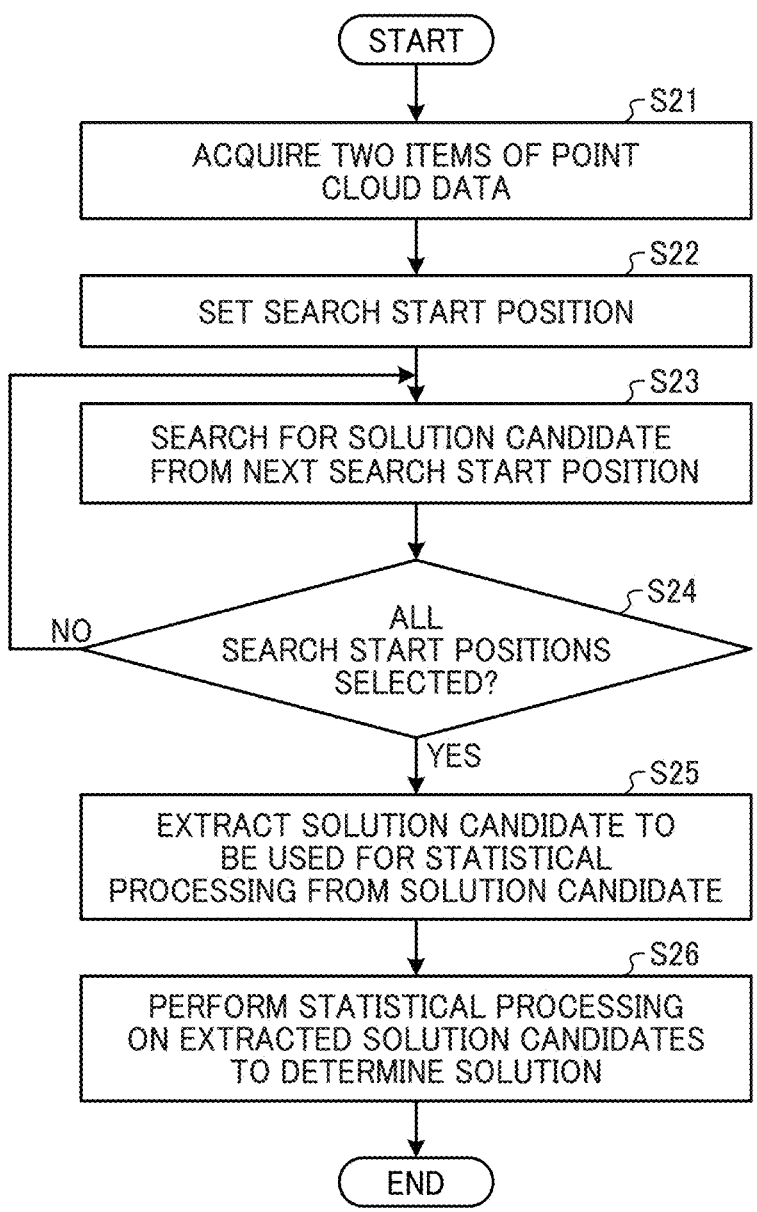
FIG. 6 is a flowchart illustrating an example alignment process, performed by the alignment apparatus, according to the second embodiment.

FIG. 6 is a flowchart illustrating an example alignment process, performed by the alignment apparatus, according to the second embodiment. Referring to FIG. 6, alignment processing by the alignment apparatus 10a according to the present embodiment will be described.

Step S21 to S23

The processes of steps S21 to S23 are the same as the processes of steps S11 to S13 illustrated in FIG. 4 in the first embodiment described above.

Step S24

The solution candidate search unit 103 determines whether all the search start positions stored in the storage unit 114 are selected or search of the solution candidate. When all the search start positions stored in the storage unit 114 are selected for the search of the solution candidate by the solution candidate search unit 103 (step S24: Yes), the operation proceeds to step S25. When there is an unselected search start position (step S24: No), the operation returns to step S23.

Step S25

The extraction unit 105 extracts a predetermined number of solution candidates from among the solution candidates searched by the solution candidate search unit 103. The operation of extracting is performed as described above. The operation then proceeds to step S26.

Step S26

The solution determination unit 104 performs statistical processing on the solution candidates extracted by the extraction unit 105, and determines a final solution from among the solution candidates. The display control unit 112 may display the final solution determined by the solution determination unit 104 on the display unit 113. Alternatively, the display control unit 112 may display point cloud data, generated by applying coordinate transformation to one of the two point cloud data using the solution determined by the solution determination unit 104, and the other point cloud data serving as the alignment target, while superimposing one above the other. The alignment process then ends.

As described above, at the alignment apparatus 10a according to the present embodiment, the extraction unit 105 extracts a predetermined number of solution candidates, from among a plurality of solution candidates searched by the solution candidate searching unit 103. The solution determination unit 104 applies statistical processing to the solution candidates, which are extracted, to determine a final solution. According to the second embodiment, in addition to the advantageous effect as that of the first embodiment described above, the influence of a solution candidate having a large outlier or error on statistical processing by the solution determination unit 104 can be reduced, such that a suitable solution can be found more stably.

Third Embodiment

The alignment apparatus according to the third embodiment will be described, focusing on differences from the alignment apparatus 10 according to the first embodiment. In the present embodiment, it is assumed that alignment processing is performed on point cloud data obtained by measuring with the measuring device. The functional configuration of the alignment apparatus according to the present embodiment is the same as that of the alignment apparatus 10 according to the first embodiment.

Hardware Configuration of Alignment Apparatus

Figure 7:
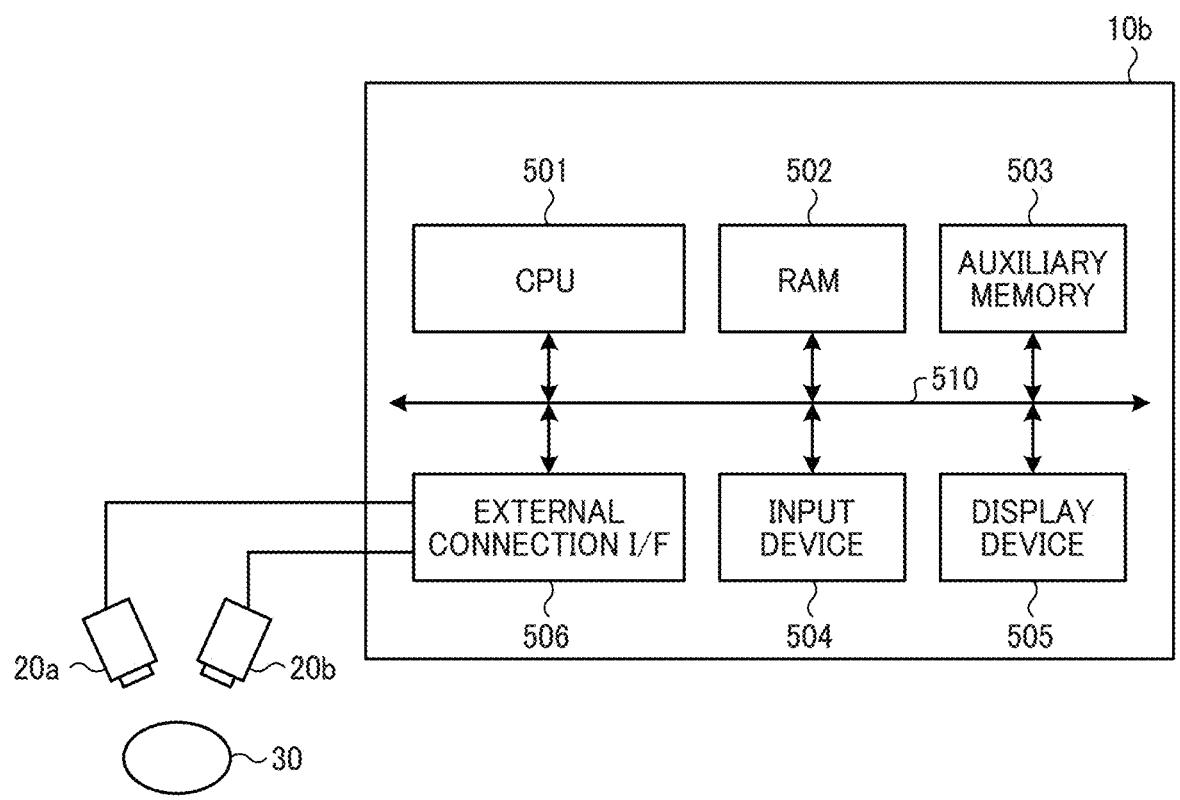
FIG. 7 is a diagram illustrating an example hardware configuration of an alignment apparatus according to a third embodiment.

FIG. 7 is a diagram illustrating an example hardware configuration of an alignment apparatus according to the third embodiment of the present invention. Referring to FIG. 7, a hardware configuration of the alignment apparatus 10b according to the present embodiment will be described.

The alignment apparatus 10b illustrated in FIG. 7 is an example of information processing apparatus that performs alignment of two sets of point cloud data of a measurement target object 30, respectively measured by measuring devices 20a and 20b. As illustrated in FIG. 7, the alignment apparatus 10b includes a CPU 501, a RAM 502, an auxiliary memory 503, an input device 504, a display device 505, and an external connection I/F 506. The functions of the CPU 501, the RAM 502, the auxiliary memory 503, the input device 504, and the display device 505 are the same as those described in the first embodiment.

The external connection I/F 506 is an interface for connecting the alignment apparatus 10b to an external device such as the measuring device 20a or 20b to enable transmission of data. The external connection I/F 506 may be, for example, an interface based on the Universal Serial Bus (USB) standard or an interface based on the Transmission Control Protocol (TCP)/Internet Protocol (IP) corresponding to ETHERNET.

The CPU 501, the RAM 502, the auxiliary memory 503, the input device 504, the display device 505, and the external connection I/F 506 are communicably connected to each other by a bus 510 such as an address bus and a data bus.

The hardware configuration of the alignment apparatus 10b illustrated in FIG. 7 is just one example, and the alignment apparatus 10b may not include all of the components illustrated in FIG. 7, or may include any other hardware components.

The measuring devices 20a and 20b are each a device that obtains point cloud data by measuring the measurement target object 30. For example, the measuring devices 20a and 20b may each be a device such as a digitizer, a laser scanner, or a stereo camera. The measuring devices 20a and 20b, which are connected to the external connection I/F 506, each outputs the point cloud data obtained by measurement to the external connection I/F 506.

Further, in the configuration illustrated in FIG. 7, the two measuring devices 20a and 20b are connected to the alignment apparatus 10b, but the configuration is not limited thereto. For example, only the measuring device 20a may be connected. In such case, the measuring device 20a may measure the measurement target object 30 a plurality of times to obtain a plurality of sets of point cloud data.

Alignment Processing of Alignment Apparatus

Figure 8:
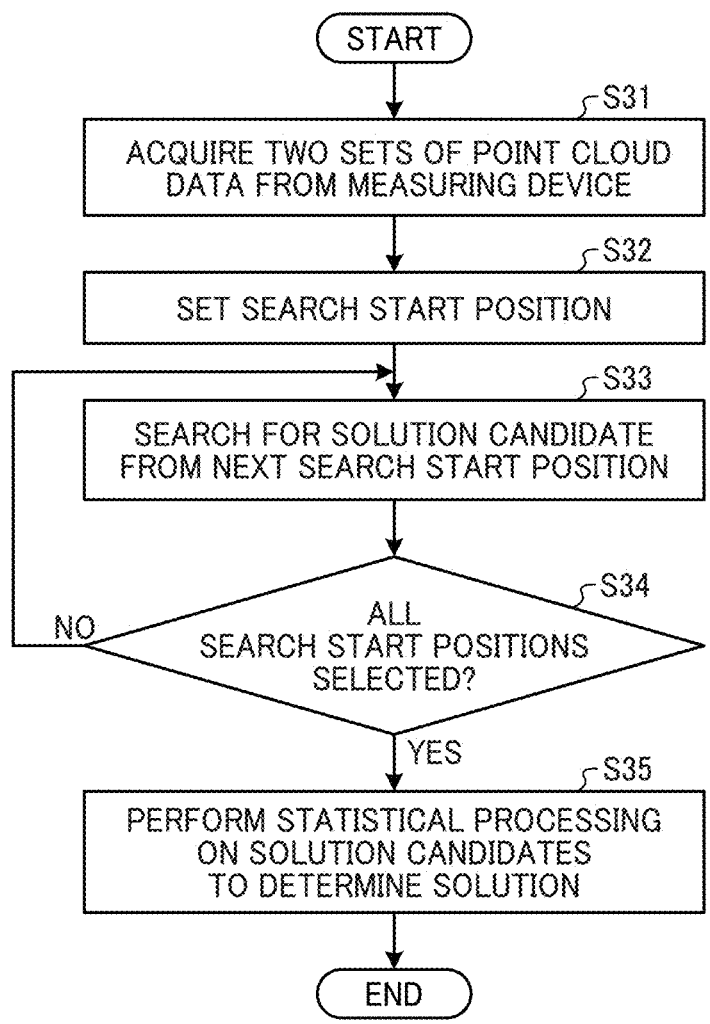
FIG. 8 is a flowchart illustrating an example alignment process, performed by the alignment apparatus, according to the third embodiment.

FIG. 8 is a flowchart illustrating an example alignment process, performed by the alignment apparatus, according to the third embodiment. Referring to FIG. 8, alignment processing by the alignment apparatus 10b according to the present embodiment will be described.

Step S31

First, the point cloud acquisition unit 101 acquires two sets of point cloud data, acquired by measuring the measurement target object 30 with the measuring devices 20a and 20b. In another example, the point cloud acquisition unit 101 may obtain two sets of point cloud data, from the measuring device 20a. In such case, the measuring device 20a may measure the measurement target object 30 a plurality of times to obtain a plurality of sets of point cloud data. The operation then proceeds to step S32.

Step S32 to S35

The processes of steps S32 to S35 are the same as the processes of steps S12 to S15 illustrated in FIG. 4 in the first embodiment described above. The alignment process then ends.

As described above, at the alignment apparatus 10b according to the present embodiment, the point cloud acquisition unit 101 uses the point cloud data obtained by the measuring devices 20a and 20b to execute the alignment process. In addition to the advantageous effect as described above in the first embodiment, there is no need to prepare the point cloud data to be used for alignment. That is, the alignment apparatus 10b in the third embodiment can perform alignment process while sequentially performing measurement on the measurement target by the measuring devices 20a and 20b.

Fourth Embodiment

The alignment apparatus according to the fourth embodiment will be described, focusing on differences from the alignment apparatus 10a according to the second embodiment. In the present embodiment, it is assumed that magnetic field distribution of a brain of a test subject (simply referred to as the subject), obtained by magnetoencephalography (MEG), is matched with a shape of the brain obtained by Magnetic Resonance Imaging (MRI). The hardware configuration of the alignment apparatus according to the present embodiment is the same as that of the alignment apparatus 10 according to the first embodiment.

Figure 9:
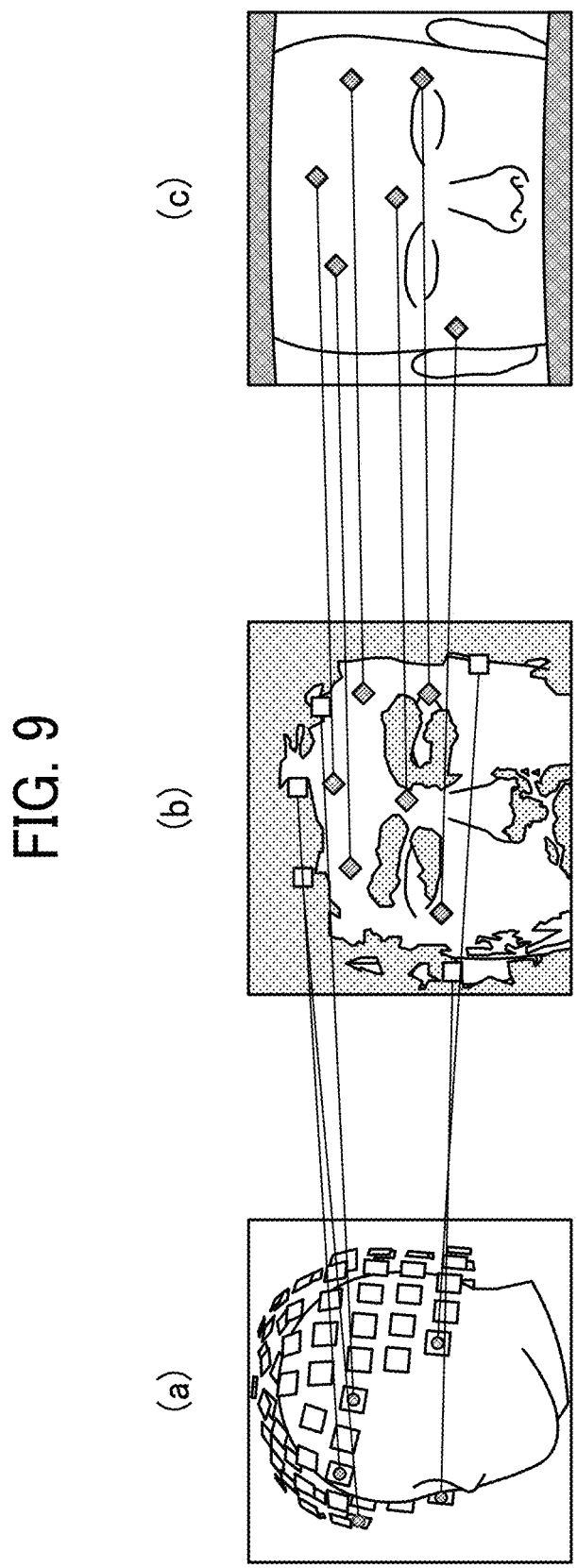
FIG. 9 is a diagram for explaining an example case in which alignment of point cloud data is used in MEG.

Overview of Processing to Match Magnetic Field Distribution of Brain With Shape of Brain in MRI FIG. 9 is a diagram for explaining a case in which alignment of point cloud data is used in MEG. Referring to FIG. 9, example processing to match the magnetic field distribution of the brain of the subject, obtained by the MEG, with the shape of the brain of the subject, obtained by the MRI, is described.

In view of multi-modality information integration in the medical field, there is a need for matching between the magnetic field distribution of the brain of a subject, obtained by a MEG, and the shape of the brain obtained by MRI, to make analysis. The method described referring to FIG. 9 may be applied.

First, using a three dimensional measuring device such as a digitizer or a laser scanner, the shape of the head of a subject wearing a coil to obtain point cloud data (hereinafter, may be referred to as scan point cloud data). The coil, worn by the subject, generates a magnetic field that is measurable by MEG, to obtain information on position and posture, which is used to generate the point cloud data. Then, the positional relationship between the position of each coil and the position of the scan point cloud data is determined. Here, a coordinate system of the scan point cloud data obtained by measurement by the three dimensional measuring device is referred to as a scan coordinate system. Accordingly, the positional relationship between the magnetic field distribution of the brain obtained by MEG and the scan point cloud data obtained by the three dimensional measuring device is determined.

With MRI, an image of the brain of the subject is obtained. Further, with MRI, point cloud data of the shape of the head of the subject (hereinafter, may be referred to as MRI point cloud data) is obtained. Here, a coordinate system of the MRI point cloud data obtained by measurement by MRI is referred to as an MRI coordinate system. Then, the alignment apparatus 10c according to the present embodiment described later performs alignment processing to align between the scan point cloud data in the scan coordinate system and the MRI point cloud data in the MRI coordinate system. This determines the positional relationship between the magnetic field distribution of the brain for which the positional relationship with the scan point cloud data is determined, and the shape of the brain for which the positional relationship with the MRI point cloud data is determined. That is, the magnetic field distribution of the brain of the subject, obtained by MEG, is matched with (superimposed on) the shape of the brain of the subject, obtained by MRI.

The alignment process by the alignment apparatus 10c according to the present embodiment may use, for example, an ICP algorithm. Evaluation is performed using point cloud data acquired under various conditions. In many cases, a solution candidate (coordinate transformation) that minimizes an error function in the ICP algorithm can be used. However, there are some cases where the obtained solution candidate is not appropriate. In the evaluation, a solution (coordinate transformation) derived from alignment between the scan point cloud data and the MRI point cloud data of the shape of the head, was compared with the position of an anatomical reference point (an example of a reference point) acquired at a same time with the shape of the head. The result was evaluated based on an error in alignment with respect to the anatomical reference point. There is a case where the error in the anatomical reference point is large although the error in the ICP algorithm is sufficiently small. As one possible reason, the error of the inappropriate solution candidate is estimated to be unreasonably small due to the pseudo correspondence of the point cloud data, so that an erroneous coordinate transformation is derived.

In this embodiment, based on hypothesis that the global optimal solution has a wider distribution than the local solution in the solution space, a final selection is determined to be either a solution candidate having the highest appearance frequency, or a solution with an error value having the highest appearance frequency (i. e., having a broad area in the solution space), from among solution candidates obtained using various search start positions.

This can hardly fall into a local solution, thus obtaining a suitable solution more stably than before. In the following, the functional configuration and operation of the alignment apparatus 10c according to the present embodiment will be described.

Functional Configuration and Operation of Alignment Apparatus

Figure 10:
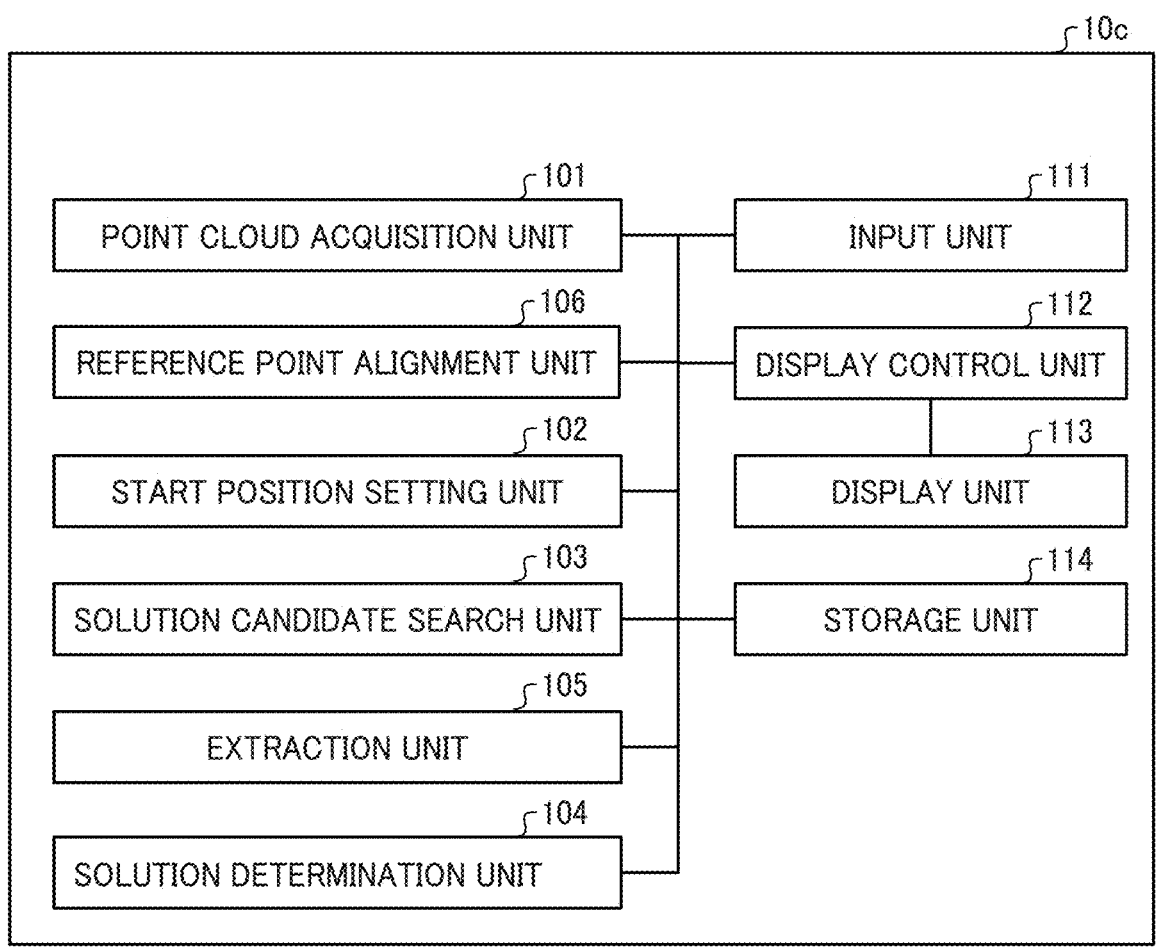
FIG. 10 is a diagram illustrating an example functional configuration of the alignment apparatus according to a fourth embodiment.

FIG. 10 is a diagram illustrating an example functional configuration of the alignment apparatus 10c according to the fourth embodiment. The functional configuration and operation of the alignment apparatus 10c according to the present embodiment will be described with reference to FIG. 10.

As illustrated in FIG. 10, the alignment apparatus 10c includes a point cloud acquisition unit 101 (acquisition unit), a reference point alignment unit 106, a start position setting unit 102 (position setting unit), a solution candidate search unit 103 (search unit), an extraction unit 105, a solution determination unit 104, an input unit 111, a display control unit 112, a display unit 113, and a storage unit 114. Of the functional units described above, the functions of the extraction unit 105, the input unit 111, the display control unit 112, the display unit 113, and the storage unit 114 are the same as those described in the second embodiment.

The point cloud acquisition unit 101 is a functional unit that reads out and acquires, from the storage unit 114, scan point cloud data (an example of first point cloud data) of the shape of the head of the subject, which is measured using the three dimensional measuring device. The point cloud acquisition unit 101 reads out and acquires, from the storage unit 114, position data (hereinafter, may be referred to as scan anatomical reference point data) (an example of first reference point data) of the anatomical reference point of the subject, which is measured by the three dimensional measuring device. In this example, as the anatomical reference point, three points of the nasal root (Nasion), the left preauricular point (LPA), and the right preauricular point (RPA) of the subject are used, but any other point may be used as the anatomical reference point. As in the third embodiment described above, the point cloud acquisition unit 101 may acquire the scan point cloud data and the scan anatomical reference point data directly from the three dimensional measuring device, instead of reading such data from the storage unit 114.

The point cloud acquisition unit 101 reads and acquires, from the storage unit 114, MRI point cloud data (an example of second point cloud data) of the shape of the head of the subject, obtained by MRI. The point cloud acquisition unit 101 reads and acquires, from the storage unit 114, position data (hereinafter, may be referred to as MRI anatomical reference point data) (an example of second reference point data) of the anatomical reference point of the subject obtained by MRI. The anatomical reference point for MRI is determined in a substantially similar manner as described above for the scan anatomical reference point data. Any method may be used to extract the MRI point cloud data. For example, a method may be used in which all MRI data is binarized and contour points on the outermost periphery are extracted. The position of the anatomical reference point may be selected by an operation input by the user via the input unit 111, or may be automatically detected using template matching or machine learning.

The point cloud acquisition unit 101 is implemented by a program executed by the CPU 501 of FIG. 1.

The reference point alignment unit 106 is a functional unit that uses the scan anatomical reference point data and the MRI anatomical reference point data, acquired by the point cloud acquisition unit 101, to perform alignment (hereinafter, may be referred to as coarse alignment) between those data sets, while maintaining the correspondence relationship between the respective points in the data sets. That is, the reference point alignment unit 106 obtains a coarse coordinate transformation Tcoarse, for transformation (alignment) from the scan anatomical reference point data to the MRI anatomical reference point data. The reference point alignment unit 106 is implemented by a program executed by the CPU 501 illustrated in FIG. 1, for example.

The start position setting unit 102 is a functional unit that sets a plurality of search start positions by each applying an offset having a preset step size to each point in the coarse coordinate transformation Tcoarse, obtained by the reference point alignment unit 106. When the coarse coordinate transformation Tcoarse is applied to the scan point cloud data in advance, the search start position may be set with reference to 0. The start position setting unit 102 is implemented by, for example, a program executed by the CPU 501 illustrated in FIG. 1.

The solution candidate search unit 103 is a functional unit that searches for a solution candidate by performing alignment using the preset alignment algorithm, starting from the search start position set by the start position setting unit 102. In this example, the solution candidate search unit 103 uses the ICP algorithm to search for a solution candidate (coordinate transformation) that minimizes the error function represented by the least square error of the position between the point cloud data. The solution candidate search unit 103 is implemented by a program executed by the CPU 501 illustrated in FIG. 1, for example.

The solution determination unit 104 is a functional unit that performs statistical processing on the solution candidates extracted by the extraction unit 105, and determines a final solution from among the solution candidates. In statistical processing, the solution determination unit 104 may determine, as a fine coordinate transformation Tfine, a solution candidate with the value (error) of the corresponding error function having the highest appearance frequently, from among a plurality of solution candidates. When there are more than one coordinate transformation with the most frequent error value, a coordinate transformation having a smaller error value may be employed. When there is a plurality of different coordinate transformations for the same error, a coordinate transformation having the smallest degree of coordinate transformation (for example, having the largest trace of a coordinate transformation matrix) may be employed. In statistical processing, the solution determination unit 104 may determine, as a fine coordinate transformation Tfine, a solution candidate having the highest appearance frequently, from among a plurality of solution candidates. Further, the solution determination unit 104 may sort the solution candidates in ascending order of values of error, and extract a predetermined number of solution candidates in order from the one having the smallest error. The solution determination unit 104 then determines, as a fine coordinate transformation Tfine, a solution candidate with the corresponding error having the highest appearance frequency, or a solution candidate having the highest appearance frequency. Then, the solution determination unit 104 determines a Tfine×Tcoarse, which is obtained by multiplying the coarse coordinate transformation Tcoarse obtained by the reference point alignment unit 106 by the fine coordinate transformation Tfine, as a coordinate transformation Tfinal that is a final solution.

At least one of the point cloud acquisition unit 101, the reference point alignment unit 106, the start position setting unit 102, the solution candidate search unit 103, the extraction unit 105, the solution determination unit 104, and the display control unit 112 may be implemented by an integrated circuit such as an ASIC or FPGA.

FIG. 10 is a conceptual diagram illustrating functional units of the alignment apparatus 10c, such that the functions of the alignment apparatus 10c is not limited to such configuration. For example, any combination of functional units, each described as an independent functional unit, in the alignment apparatus 10c illustrated in FIG. 10 may be configured as one functional unit. Alternatively, functions performed by one functional unit of the alignment apparatus 10c illustrated in FIG. 10 may be divided into a plurality of functions to constitute a plurality of functional units.

Alignment Processing of Alignment Apparatus

FIG. 11 is a flowchart illustrating an example alignment process, performed by the alignment apparatus, according to the fourth embodiment. Referring to FIG. 11, alignment processing by the alignment apparatus 10c according to the present embodiment will be described.

Step S41

The point cloud acquisition unit 101 reads out and acquires, from the storage unit 114, scan point cloud data of the shape of the head of the subject, which is measured using the three dimensional measuring device, and the scan anatomical reference point data of the subject. The operation then proceeds to step S42.

Step S42

The point cloud acquisition unit 101 reads and acquires, from the storage unit 114, MRI point cloud data of the shape of the head of the subject obtained by MRI, and MRI anatomical reference point data of the subject. The processing order of step S41 and step S42 is not limited thereto, and may be reversed. The operation then proceeds to step S43.

Step S43

The reference point alignment unit 106 uses the scan anatomical reference point data and the MRI anatomical reference point data, acquired by the point cloud acquisition unit 101, to perform alignment between those data sets, while maintaining the correspondence relationship between the respective points in the data sets. That is, the reference point alignment unit 106 obtains a coarse coordinate transformation Tcoarse, for transformation from the scan anatomical reference point data to the MRI anatomical reference point data. In the alignment process, the error in alignment of the anatomical reference point becomes an objective function, and the objective function is minimized.

In another example, the processing of S43 may be omitted. Alternatively, the alignment apparatus 10c may request the user to manually perform rough alignment via the input unit 111 and the display unit 113. When this step is omitted, the coarse coordinate transformation Tcoarse becomes a unit matrix. The operation then proceeds to step S44.

Step S44

The start position setting unit 102 sets a plurality of search start positions by each applying an offset having a preset step size to each point in the coarse coordinate transformation Tcoarse, obtained by the reference point alignment unit 106. Then, the start position setting unit 102 stores the set search start position in the storage unit 114. The operation then proceeds to step S45.

Step S45

The solution candidate search unit 103 reads, from the storage unit 114, a search start position that has not been selected, from among the search start positions set by the start position setting unit 102, and performs alignment from the search start position using the preset alignment algorithm to search for a solution candidate. In this example, the solution candidate search unit 103 uses the ICP algorithm to search for a solution candidate (coordinate transformation) that minimizes the error function represented by the least square error of the position between the point cloud data. The solution candidate search unit 103 stores, in the storage unit 114, the searched solution candidate and the value of the error function in association with each other. The operation then proceeds to step S46.

Step S46

The solution candidate search unit 103 determines whether all the search start positions stored in the storage unit 114 are selected or search of the solution candidate.

When all the search start positions stored in the storage unit 114 are selected for the search of the solution candidate by the solution candidate search unit 103 (step S46: Yes), the operation proceeds to step S47. When there is an unselected search start position (step S46: No), the operation returns to step S45.

Step S47

The extraction unit 105 extracts a predetermined number of solution candidates from among the solution candidates searched by the solution candidate search unit 103. The operation of extracting is performed as described above in the second embodiment. This step is not essential, and may be skipped. The operation then proceeds to step S48.

Step S48

In statistical processing, the solution determination unit 104 may determine, as a fine coordinate transformation Tfine, a solution candidate with the value (error) of the corresponding error function having the highest appearance frequently, from among a plurality of solution candidates.

When there are more than one coordinate transformations with the highest frequent error value, a coordinate transformation having a smaller error value may be employed. When there is a plurality of different coordinate transformations for the same error, a coordinate transformation having the smallest degree of coordinate transformation (for example, having the largest trace of a coordinate transformation matrix) may be employed. The operation then proceeds to step S49.

Step S49

Then, the solution determination unit 104 determines a Tfine×Tcoarse, which is obtained by multiplying the coarse coordinate transformation Tcoarse obtained by the reference point alignment unit 106 by the fine coordinate transformation Tfine, as a coordinate transformation Tfinal that is a final solution. The operation then proceeds to step S50.

Step S50

The display control unit 112 applies the coordinate transformation Tfinal determined by the solution determination unit 104 to the scan point cloud data and the scan anatomical reference point data to generate the scan point cloud data and the scan anatomical reference point data, which are aligned. The display control unit 112 displays the aligned scan point cloud data and scan anatomical reference point data, and the MRI point cloud data and MRI anatomical reference point data, on the display unit 113, with different colors but one above the other. If the user is not satisfied with the alignment result displayed on the display unit 113, the user may change the search start position via the input unit 111 to instruct the alignment apparatus to execute alignment processing again. The alignment process then ends.

As described above, the alignment apparatus 10c according to the present embodiment aligns between the magnetic field distribution of the brain of the subject, obtained by MGE, and the shape of the brain obtained by MRI. Specifically, the above-described alignment processing is applied to point cloud data respectively obtained by the three dimensional measuring device and MRI. With this configuration, a solution suitable to coordinate transformation from the coordinate system of the three dimensional measuring device (scan coordinate system), to the MRI coordinate system can be found more stably.

The above-described two-stage processing including the coarse alignment using the reference point and the fine alignment using the point cloud data is not limited to the multi-modality information integration application in the medical field, such that this two-stage processing may be applied to any other field.

In the alignment process according to the present embodiment, the coarse coordinate transformation Tcoarse and the fine coordinate transformation Tfine are separately obtained, but the present invention is not limited thereto. For example, the start position setting unit 102 may set a plurality of search start positions based on the coarse coordinate transformation Tcoarse obtained by the reference point alignment unit 106. In such case, since the fine coordinate transformation Tfine determined by the solution determination unit 104 has some effects similar to those provided by the coarse coordinate transformation Tcoarse, it can be regarded as the coordinate transformation Tfinal.

In each of the above-described embodiments, the solution determination unit 104 performs statistical processing on the values of the objective function corresponding to the plurality of solution candidates, and determines the final solution based on the result of the statistical processing. However, the present invention is not limited thereto. As described above, the solution determination unit 104 may perform statistical processing on a plurality of solution candidates themselves, to determine a final solution. For example, the solution determination unit 104 may obtain appearance frequencies of solution candidates, and determine a solution candidate having the highest appearance frequency as a final solution.

Each of the functions of the above-described embodiments may be implemented by one or more processing circuits or circuitry. Processing circuitry includes a programmed processor, as a processor includes circuitry. A processing circuit also includes devices such as an application specific integrated circuit (ASIC), a digital signal processor (DSP), a field programmable gate array (FPGA), a system on a chip (SOC), a graphics processing unit (GPU), and conventional circuit components arranged to perform the recited functions.

In any one of the embodiments described above, when at least one of the functional units of the alignment apparatus 10 (10a to 10c) is implemented by a program executed by the CPU, such program may be installed in a ROM or any desired memory of the alignment apparatus 10 in advance. The program executed by the alignment apparatus 10 (10a to 10c) according to any one of the above-described embodiments may be stored in a computer-readable recording medium such as a compact disc read only memory (CD-ROM), a flexible disk (FD), a compact disk-recordable (CD-R), a digital versatile disk (DVD), or a secure digital (SD) card in an installable or executable file format. The program executed by the alignment apparatus 10 (10a to 10c) according to any one of the above-described embodiments may be stored in a computer connected to a network such as the Internet, such that the program can be downloaded via the network. The program executed by the alignment apparatus 10 (10a to 10c) according to any one of the above-described embodiments may be provided or distributed via a network such as the Internet. The program executed by the alignment apparatus 10 (10a to 10c) according to any one of the above-described embodiments has a module configuration including at least one of the above-described functional units. As a CPU reads the program from the above-described memory and executes the program, each of the above-described functional units is loaded onto the main memory (work area) to operate as the functional unit.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

Any one of the above-described operations may be performed in various other ways, for example, in an order different from the one described above.

The invention claimed is:

1. An alignment apparatus comprising circuitry configured to:
   acquire first point cloud data and second point cloud data, the second point cloud data being different from the first point cloud data;
   set a plurality of search start positions;
   search for a respective solution candidate with respect to each of the plurality of search start positions to generate a plurality of solution candidates, each of the plurality of solution candidates corresponding to a respective coordinate transformation from the first point cloud data to the second point cloud data; and determine a final solution for alignment from the first point cloud data to the second point cloud data based on the plurality of solution candidates.

2. The alignment apparatus of claim 1, wherein the circuitry is configured to performs statistical processing on the one or more of the plurality of solution candidates based on values of an objective function corresponding to the one or more of the plurality of solution candidates.

3. The alignment apparatus of claim 2, wherein the circuitry is configured to perform the statistical processing including determining a first solution candidate among the plurality of solution candidates to correspond to the final solution based on the first solution candidate having a first value of the objective function that appears most frequently among values of the objective function corresponding to the one or more of the plurality of solution candidates.

4. The alignment apparatus of claim 2, wherein the circuitry is configured to:
extract a predetermined number of solution candidates from among the plurality of solution candidates; and
determine the final solution including performing the statistical processing the predetermined number of solution candidates.

5. The alignment apparatus of claim 4, wherein the circuitry is configured to extracts the predetermined number of solution candidates; in ascending order of a respective value of the objective function corresponding to each of the predetermined number of solution candidates.

6. The alignment apparatus of claim 1, wherein the circuitry is configured to determine a second solution candidate among the plurality of solution candidates to correspond to the final solution based on the second solution candidate having a highest appearance frequency among the plurality of solution candidates.

7. The alignment apparatus of claim 1, wherein the circuitry is configured to set the plurality of search start positions including shifting a position of the first point cloud data by a random value.

8. The alignment apparatus of claim 1, wherein the circuitry is configured to set the plurality of search start positions including shifting position of the first point cloud data by a predetermined offset value.

9. The alignment apparatus of claim 1, further comprising:
a memory that stores the first point cloud data and the second point cloud data,
wherein the circuitry is configured to acquire the first point cloud data and the second point cloud data by reading out the first point cloud data and the second point cloud data from the memory.

10. The alignment apparatus of claim 1, wherein the circuitry is configured to acquires the first point cloud data and the second point cloud data from one or more three-dimensional measuring devices that measure the first point cloud data and the second point cloud data.

11. The alignment apparatus of claim 1, wherein the circuitry is configured to:
acquire first reference point data corresponding to a plurality of reference points for the first point cloud data in a first coordinate system;
acquire second reference point data corresponding to a plurality of reference points for the second point cloud data in a second coordinate system;
determine a coordinate transformation for alignment from the first reference point data to the second reference point data; and determine the final solution using the coordinate transformation.

12. The alignment apparatus of claim 11, wherein the circuitry is configured to:
perform statistical processing on the one or more of the plurality of solution candidates based on values of an objective function corresponding to the one or more of the plurality of solution candidates to determine a third solution candidate among the plurality of solution candidates; and
determine the final solution including multiplying the third solution candidate by the coordinate transformation.

13. The alignment apparatus of claim 11, wherein the circuitry is configured to set the plurality of search start positions based on the coordinate transformation.

14. The alignment apparatus of claim 1, wherein the circuitry is configured to display a result of the alignment from the first point cloud data to the second point cloud data on a display.

15. The alignment apparatus of claim 1, wherein each of the plurality of solution candidates corresponds to a respective candidate displacement vector and a respective candidate rotation matrix.

16. The alignment apparatus of claim 1, wherein the circuitry is configured to search for the respective solution candidate with respect to each of the plurality of search start positions such that the respective solution candidate minimizes an objective function.

17. An alignment system comprising circuitry configured to:
acquire first point cloud data and second point cloud data, the second point cloud data being different from the first point cloud data;
set a plurality of search start positions;
search for a respective solution candidate with respect to each of the plurality of search start positions to generate a plurality of solution candidates, each of the plurality of solution candidates corresponding to a respective coordinate transformation from the first point cloud data to the second point cloud data; and
determine a final solution for alignment from the first point cloud to the second point cloud data based on the plurality of solution candidates.

18. The alignment system of claim 17, further comprising:
one or more three-dimensional measuring devices configured to measure the first cloud point data and the second cloud point data,
wherein the circuitry is configured to acquire the first cloud point data and the second cloud point data from the one or more three-dimensional measuring devices.

19. An alignment method comprising:
acquiring first point cloud data and second point cloud data, the second point cloud data being different from the first point cloud data;
setting a plurality of search start positions;
searching for a respective solution candidate with respect to each of the plurality of search start positions to generate a plurality of solution candidates, each of the plurality of solution candidates corresponding to a respective coordinate transformation from the first point cloud data to the second point cloud data; and
determining a final solution for alignment from the first point cloud data to the second point cloud data based on the plurality of solution candidates.

20. A non-transitory recording medium storing instructions which, when executed by one or more processors, cause the processors to perform an alignment method comprising:
- acquiring first point cloud data and second point cloud data, the second point cloud data being different from the first point cloud data;
- setting a plurality of search start positions;
- searching for a respective solution candidate with respect to each of the plurality of search start positions to generate a plurality of solution candidates, each of the plurality of solution candidate corresponding to a respective coordinate transformation from the first point cloud data to the second point cloud data; and
- determining a final solution for alignment from the first point cloud data to the second point cloud data based on the plurality of solution candidates.

* * * * *